United States Patent
Crainich

[11] Patent Number: 5,562,681
[45] Date of Patent: Oct. 8, 1996

[54] STAPLE REMOVER

[76] Inventor: Lawrence Crainich, Ceda Rd., P.O. Box 996, Charlestown, N.H. 03603

[21] Appl. No.: 331,066

[22] Filed: Oct. 28, 1994

[51] Int. Cl.⁶ .................................................. A61B 17/00
[52] U.S. Cl. ............................................. 606/138; 254/28
[58] Field of Search ...................... 606/138, 75; 254/28; 227/175–176; 81/419, 421, 422, 342, 381, 420

[56] References Cited

U.S. PATENT DOCUMENTS

| | | |
|---|---|---|
| 3,254,649 | 6/1966 | Wood . |
| 3,283,557 | 11/1966 | Wood . |
| 3,344,649 | 10/1967 | Wood . |
| 3,817,078 | 6/1974 | Reed et al. . |
| 3,960,147 | 6/1976 | Murray .................................. 606/75 |
| 4,026,520 | 5/1977 | Rothfuss et al. . |
| 4,640,274 | 2/1987 | Nakamoto ............................. 606/138 |
| 4,944,295 | 7/1990 | Gwathmey et al. .................. 227/176 |
| 5,451,231 | 9/1995 | Rabenau et al. ..................... 606/138 |

FOREIGN PATENT DOCUMENTS

| | | | |
|---|---|---|---|
| 597/72 | 2/1968 | Japan ........................... 254/28 |
| 1563680 | 5/1990 | U.S.S.R. ..................... 606/138 |

Primary Examiner—Michael Powell Buiz
Assistant Examiner—Jeffrey A. Schmidt
Attorney, Agent, or Firm—Bachman & LaPointe, PC

[57] ABSTRACT

A staple remover is disclosed for removing surgical staples wherein said surgical staples have side members spaced from each other in a fired position at a staple spacing. The staple remover has a housing, a first arm having a first end and a second arm having a second end, said first and second arms being positioned within said housing so that said first and second ends extend from said housing at a first spacing which is less than said staple spacing, and a widening member for widening said first spacing of said first and second ends to a second spacing wider than said staple spacing.

21 Claims, 4 Drawing Sheets

STAPLE REMOVER

BACKGROUND OF THE INVENTION

The invention relates to an improved staple remover or extractor for removing staples, especially surgical staples and the like.

Numerous devices are known for use in removing surgical staples. For example, U.S. Pat. No. 4,026,520 to Rothfuss et al. discloses a surgical staple extractor which crimps or bends the base or bail portion of a typical surgical staple so as to open the arms of the staple thereby freeing the staple from the skin segments or other tissue in which the staple is placed so as to free the staple for removal. Such an apparatus is useful for removing conventional staples. However, when the bail or base portion of the staple is not straight, either by design or due to twisting or other distortion of the staple which may occur during placement thereof, a staple extractor such as that disclosed by Rothfuss et al. is likely to cause the staple to twist or reorient rather than open. One example of surgical staples having a bail portion which is not straight by design are those disclosed in U.S. Pat. No. 5,222,975, issued to Lawrence Crainich on Jun. 29, 1993.

Furthermore, known staple extractors such as Rothfuss et al. and others such as those disclosed in U.S. Pat. Nos. 3,817,078 to Reed et al., 3,344,649 to Wood, 3,283,557 to Wood, and 3,254,649 to Wood all disclose removers which are individual and separate devices from the surgical stapler which has been used to place the staples. Thus, such staple removers are duplicative in the number of instruments which must be prepared for use by a surgeon. Further, numerous surgical staple devices are now available for use in placing staples in positions which are not readily accessible with the hand held devices disclosed in the above-mentioned patents.

In accordance with the foregoing, it is the primary object of the present invention to provide a staple remover which is effective in removing staples having bail portions which are not necessarily straight.

It is a further object of the present invention to provide a staple remover which provides a firm grasp of a staple to be removed and which also provides reliable opening of the staple to be removed.

It is a still further object of the invention to provide a staple remover in the form of a cartridge adaptable for use with surgical stapler equipment, especially laparoscopic surgical equipment, whereby the staple remover may be readily positioned to any location where staples have been applied.

Other objects and advantages will appear hereinbelow.

SUMMARY OF THE INVENTION

The foregoing objects and advantages are readily attained by the present invention. In accordance with the invention, a staple remover is provided for removing surgical staples which typically have, in a fired position, a substantially closed or O-shaped configuration having side members spaced from each other at a staple spacing.

In accordance with the invention, a staple remover is disclosed which comprises a housing, a first arm having a first end and a second arm having a second end, said first and second arms being positioned within said housing so that said first and second ends extend from said housing at a first spacing which is less than said staple spacing, and means for widening said first spacing of said first and second ends to a second spacing wider than said staple spacing.

In further accordance with the invention, said widening means comprises a pusher member slidably positioned in said housing for longitudinal sliding between a widening position wherein said pusher member deflects said first and second arms to said second spacing and a ready position wherein said first and second arms are at said first spacing.

In further accordance with the invention, a staple remover cartridge is provided for use with a laparoscopic surgical stapler having a releasable stapler attachment and a body member for receiving said stapler attachment, said staple remover cartridge comprising a housing; staple removing means positioned within said housing; and means for releasably connecting said cartridge to said body member whereby said staple removing means is operable with said body member. In accordance with the invention, the staple remover cartridge is used with the same instrument utilized to install surgical staples.

BRIEF DESCRIPTION OF THE DRAWINGS

A detailed description of preferred embodiments of the invention follows, with reference to the attached drawings wherein.

DETAILED DESCRIPTION

Figure 1:
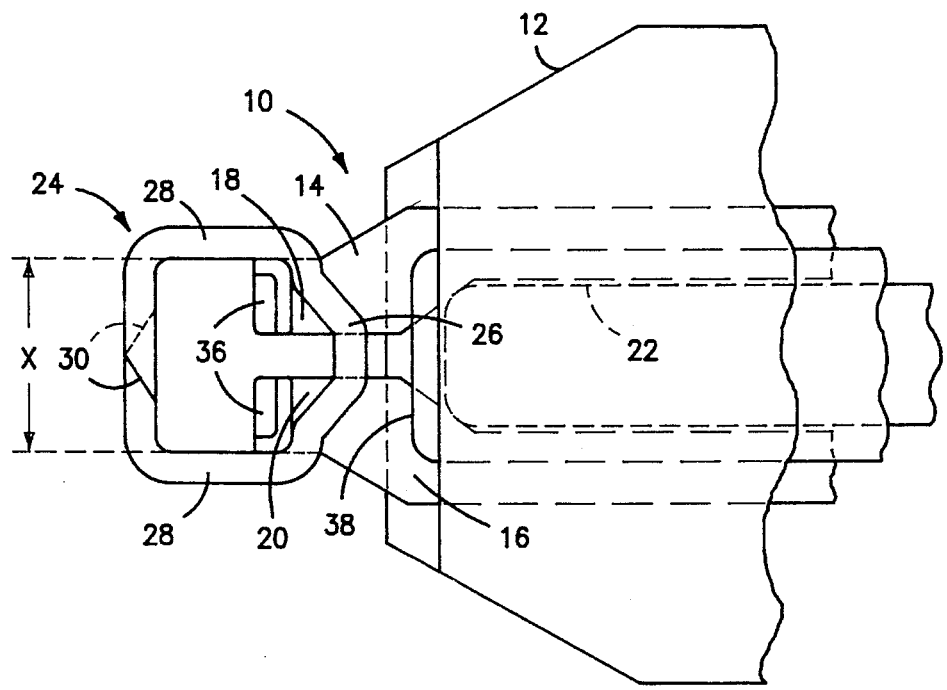
FIG. 1 is a top partially schematic view of the head portion of a staple remover in accordance with the invention and positioned for removal of a surgical staple.

The invention relates to a staple remover for removing surgical staples and the like, especially for removing surgical staples having a bail or base portion which is not straight. Referring to the accompanying drawings, a staple remover in accordance with the present invention is generally referred to by the reference numeral 10.

Figure 2:
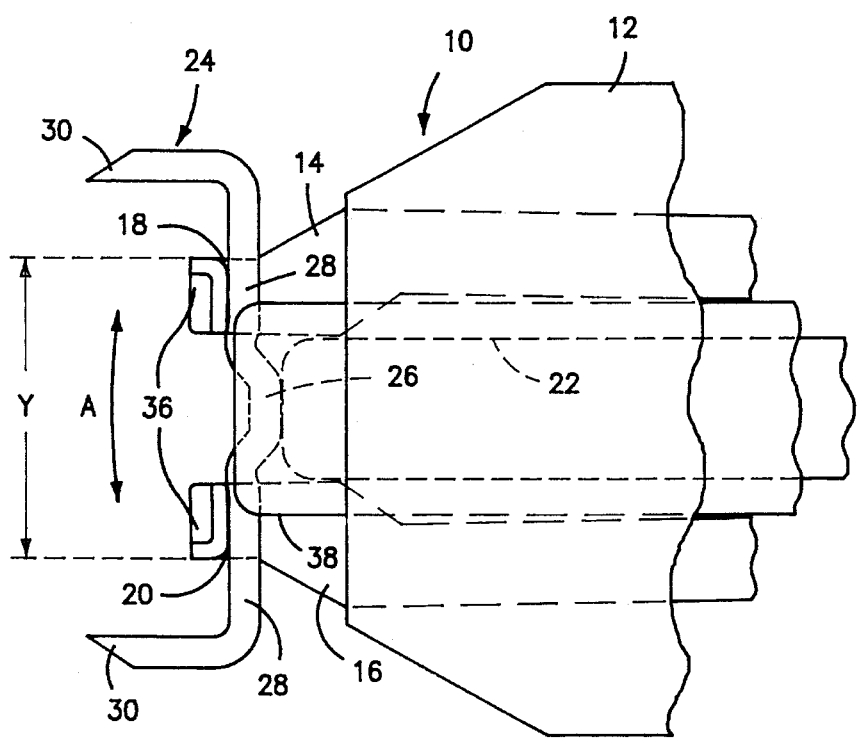
FIG. 2 is a top schematic view similar to FIG. 1 wherein the staple remover has been operated so as to remove or open a surgical staple in accordance with the invention.

FIGS. 1 and 2 schematically illustrate a portion of a staple remover 10 in accordance with the invention. Staple remover 10 preferably includes a housing 12, two arm members 14, 16 mounted within housing 12 and each having ends 18, 20 respectively protruding from housing 12 at a first spacing X (FIG. 1). Staple remover 10 further preferably includes a deflecting or widening member 22 slidably positioned within housing 12 for deflecting arms 14, 16 and respective ends 18, 20 to a wider spacing Y (FIG. 2).

In accordance with the invention, staple remover 10 is particularly useful in removing staples 24 which, in their closed position (FIG. 1) have a substantially closed or O-shaped configuration having a base or bail portion 26 which may not be straight, opposed side members 28 which are spaced from each other at a particular staple spacing, and leg or pointed portions 30 for penetrating and holding skin or other tissue to be treated with staple 24.

Prior art staple removers which act on bail portion 26 of staple 24 would be ineffective in removing staples such as those shown in FIGS. 1 and 2 because the staple would tend to twist rather than open because of the hump in bail 26. In accordance with the present invention, however, such staples are readily removed by staple remover 10. Widening member 22 serves to deflect arms 14, 16 away from each other as illustrated by arrow A in FIG. 2 so as to apply a widening or opening force to side members 28 of staple 24 and thereby open or bend staple 24 to a removable or open position as illustrated in FIG. 2. Of course, staple remover 10 in accordance with the invention is equally effective in removing staples having straight bail portions.

Figure 3:
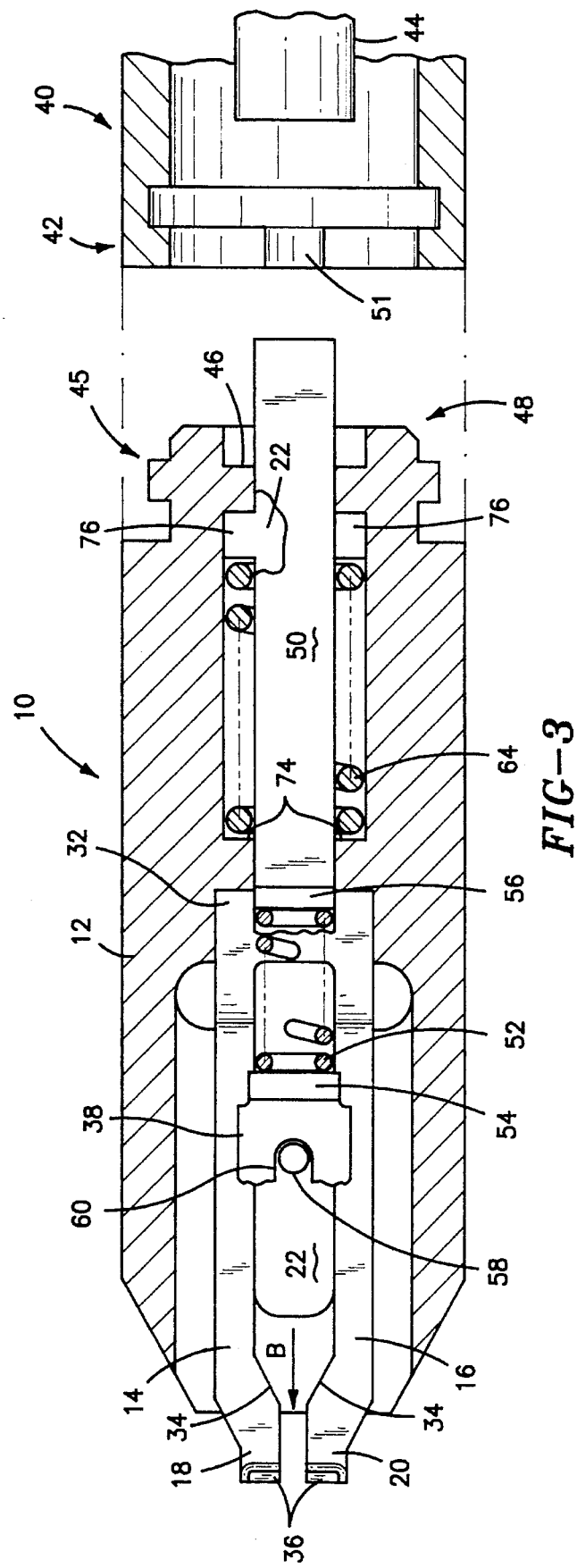
FIG. 3 is a top sectional view of a staple remover cartridge in accordance with the invention.
Figure 4:
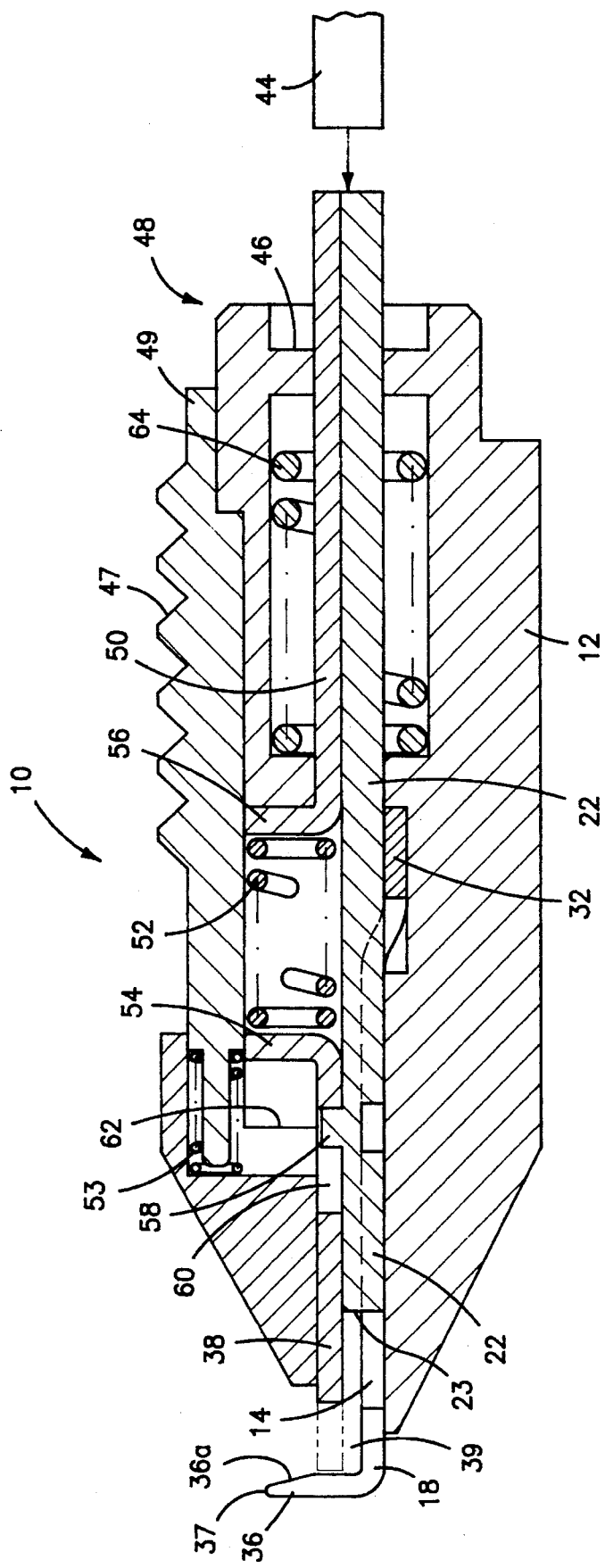
FIG. 4 is a side sectional view of a staple remover cartridge in accordance with the invention.

FIGS. 3 and 4 illustrate sectional views of a staple remover 10 in accordance with the invention. As shown, arms 14, 16 are preferably substantially elongate and flat members which are joined at a base portion 32, preferably positioned and mounted within housing 12. Arms 14, 16 are preferably joined at a spacing sufficiently small that ends 18, 20 of arms 14, 16 will fit between side members 28 of a staple 24 to be removed. In other words, spacing X (FIG. 1) is preferably less than or equal to the distance or spacing between sides 28 of a staple to be removed. Arms 14, 16 are preferably made from a resilient material which allows arms 14, 16 to be deflected away from each other to the desired wider spacing Y (FIG. 2) for the removal of staples in accordance with the invention. Alternatively, arms 14, 16 could be independent of one another and hingedly connected within housing 12 so as to allow for the desired spreading of same. In this regard, arms 14, 16 preferably have inner edges 34 facing each other and tapering toward each other as shown in FIG. 3. As will be discussed below, tapered edges 34 operate as cams or cam surfaces and interact with widening member 22 so as to provide a smooth increase in spacing of arms 14, 16 and respective ends 18, 20 when widening member 22 is advanced in housing 12.

As best shown in FIG. 4, ends 18, 20 preferably include prong portions 36 which extend, preferably at an angle of about 90° with respect arms 14, 16, so as to facilitate removal of staples in accordance with the invention. Prongs 36 preferably extend upwardly from ends 18, 20 as shown in FIG. 4. Prongs 36 further serve to maintain a removed staple on staple remover 10 for withdrawal from the site or location from which it is being removed. Thus, prongs 36 serve to provide more effective removal of staples. It should be noted, of course, that prong portions 36 may extend at other angles depending upon the desired application. Prongs 36 may preferably have tapered surfaces 36a and taper toward terminal point 37 as shown so as to facilitate entry of prongs 36 into a staple which may be embedded in tissue.

Widening member 22 is preferably a substantially elongate and flat member slidably disposed within housing 12 between arms 14, 16. Widening member 22 is preferably a pusher member which is acted upon by any conventional triggering assembly to which housing 12 may be attached. In this manner, when a staple is to be removed, widening member 22 may be forwardly displaced (See arrow B in FIG. 3) within housing 12 so as to contact tapered edges 34 and thereby deflect arms 14, 16 and respective ends 18, 20 to a wider lateral spacing wherein a staple to be removed is widened and bent to an open and removable position. Upon return or retreat of widening member 22 within housing 12, resilient arms 14, 16 preferably return to the original spacing X as shown in FIGS. 1 and 3.

In further accordance with the invention, a holding member 38 is provided for securely capturing or holding a staple 24 in place on staple remover 10 during removal. Holding member 38 is preferably an elongate substantially flat arm member slidably mounted within housing 12 between a retracted position (FIG. 1 and solid lines in FIG. 4) wherein prongs 36 may be positioned within or between side members 28 of a staple 24 to be removed, and an extended position (FIG.2 and dashed lines in FIG. 4) wherein bail 26 of a staple 24 to be removed is captured between holding member 38 and arms 14, 16. Holding member 38 is partially broken away in the illustration of FIG. 3 so as to clearly show the features, positioning and configuration of widening member 22 and tapered edges 34 of arms 14, 16 which are preferably disposed beneath holding member 38 as shown.

Referring to FIG. 4, staples to be removed are held securely by staple remover 10 in a gap 39 between holding member 38 in the forward position and the top surfaces and ends 18, 20 of arms 14, 16. Widening member 22 preferably has a thickness at forward edge 23 thereof so that widening member 22 also serves to push on bail portion 26 of a staple 24 held in gap 39 so as to assist in bending staple 24 to an open configuration. In this embodiment, staple 24 is confined or held in place by holding member 38 so as to advantageously prevent any undesirable pivot or mis-orientation of staple 24 due to pushing from widening member 22.

As illustrated in the drawings, particularly in FIGS. 3-4, widening member 22 and holding member 38 are both preferably mounted within housing 12 for longitudinal slidable positioning. Thus, in accordance with the invention, widening member 22 and holding member 38 are advantageously operable and actuated by longitudinal motion. Thus, in accordance with the invention, staple remover 10 may readily be adapted for connection to conventional stapler assemblies, especially laparoscopic assemblies, which are typically operated by longitudinal push members or rods thereby providing a staple remover 10 which is more versatile than conventional devices. As discussed above, such conventional devices are typically independent from the actual surgical stapler, and involve scissor-like or lever-like motion for operation.

Referring to FIG. 3, a portion of a laparoscopic surgical stapler is indicated by reference numeral 40. As shown, laparoscopic stapler 40 typically ends in a tubular opening having structure 42 for receiving a stapler cartridge. A push rod 44 is typically disposed within stapler 40 and actuated by a trigger mechanism at the other end (not shown in FIG. 3) of stapler 40. As shown in FIG. 3, housing 12 preferably has structure 45 which may be similar to that of the stapler cartridge to be used with stapler 40 so that staple remover 10 may be readily and releasably connected to laparoscopic stapler 40. In the embodiment shown in FIG. 3, structure 42, 45 comprises an interlocking ridge and groove configuration such as that disclosed in co-pending and commonly owned U.S. Patent application Ser. No. 08/055,639 filed Apr. 29, 1993 now U.S. Pat. No. 5,407,293. FIG. 4 also illustrates a locking element 47 of staple remover 10 which serves to releasably lock structure 45 of staple remover 10 with structure 42 of stapler 40 (FIG. 3). In this embodiment, locking element 47 has a longitudinally extending arm 49 (FIG.4) slidably mounted to housing 12 and slidable between a withdrawn position wherein structure 45 and 42 can be coupled and uncoupled as desired and an extended position wherein arm 49 extends into track 51 of structure 42 when structure 42 and structure 45 are coupled so as to lock these elements in a coupled position. Locking element 47 and arm 49 may preferably be biased toward the extended locking position by any suitable means such as spring 53 or any other suitable means.

FIG. 4 illustrates a side cross-section of staple remover 10 in accordance with the invention. As shown, widening member 22 may preferably extend rearwardly through housing 12 to an opening 46 at a rear portion 48 of housing 12. In accordance with the invention, widening member 22 thereby extends rearwardly from housing 12 for interaction with rod 44 of laparoscopic stapler 40. Also as shown in FIG. 4, holding member 38 is preferably also operated by rod 44. As best shown in FIG. 4, holding member 38 is operated by rod 44 of stapler 40 through spring 52 and a rod extension 50 which is slidably disposed within housing 12 so as to protrude from opening 46 along with widening member 22 for interaction with rod 44. As shown, rod extension 50 cooperates with holding member 38 through spring 52 or other biasing member so as to provide a desirable range of longitudinal deflection of rod extension 50 relative to holding member 38 as will be further discussed below. To this end, holding member 38 may suitably have an upwardly directed end portion 54, and rod extension 50 may have an upwardly directed front portion 56, with spring 52 disposed therebetween as shown.

It is noted that rod extension 50 is preferably mounted in substantially parallel close proximity with widening member 22 so that both elements are operated as desired by rod 44. In this regard, it is noted that widening member 22 preferably has a longer range of motion than holding member 38. Thus, in accordance with the invention, widening member 22 is preferably slidably mounted relative to holding member 38 so that widening member 22 has a range of additional forward motion beyond the forward position of holding member 38. To this end, in accordance with the invention, widening member 22 preferably has an upstanding projection or knob 58 and holding member 38 preferably has a slot 60 into which knob 58 extends. Slot 60 has a longitudinal length selected in accordance with a desired range of additional motion of widening member 22 relative to holding member 38. The above described structure, in conjunction with spring 52 disposed between holding member 38 and rod extension 50, provide desirable operation of staple remover 10 in accordance with the invention. In operation, rod 44 of stapler 40 is pushed or urged against the ends of rod extension 50 and widening member 22 so as to deflect both in a forward direction relative to housing 12. This results in widening member 22 being forwardly urged, and in rod extension 50 forwardly displacing holding member 38 via spring 52. When holding member 38 reaches the position as shown in dashed lines in FIG. 4, holding member 38 is held against further forward displacement by either or both of contact with an inner wall portion 62 of housing 12 or contact with prongs 36. At this point, further forward urging of rod 44 will result in compression of spring 52 between holding member 38 and rod extension 50, and the completion of the forward motion of widening member 22 so as to contact tapered edges 34 and deflect arms 14, 16 away from each other so as to widen ends 18, 20 and thereby open and remove the staple which is being acted upon. As set forth above, slot 60 in holding member 38 is preferably selected in accordance with the invention having a length sufficient to allow the remaining required forward motion of widening member 22 relative to holding member 38.

In further accordance with the invention, and as shown in FIGS. 3 and 4, a biasing member or spring 64 is preferably arranged within housing 12 so as to bias widening member 22 and rod extension 50 toward a rearward starting position. As shown in FIG. 3, biasing member 64 may suitably be arranged or positioned around member 22 between a stop structure 74 within housing 12 and one or more ears 76 extending laterally from rod 22. Thus, when a staple has been completely removed, and rod 44 is withdrawn from contact with the ends of widening member 22 and rod extension 50, biasing member 64 returns the elements of staple remover 10 to a starting or ready position for removal of the next staple. In this regard, it should be noted that holding member 38 may advantageously be used in accordance with the invention to contain a removed staple in staple remover 10 until the staple has been completely removed from its prior site of application. This may readily be accomplished by maintaining rod 44 and, thereby, holding member 38 via spring 52 in the forward position until it is desirable to remove the extracted staple from its position on ends 18, 20 of arms 14, 16.

Figure 5:
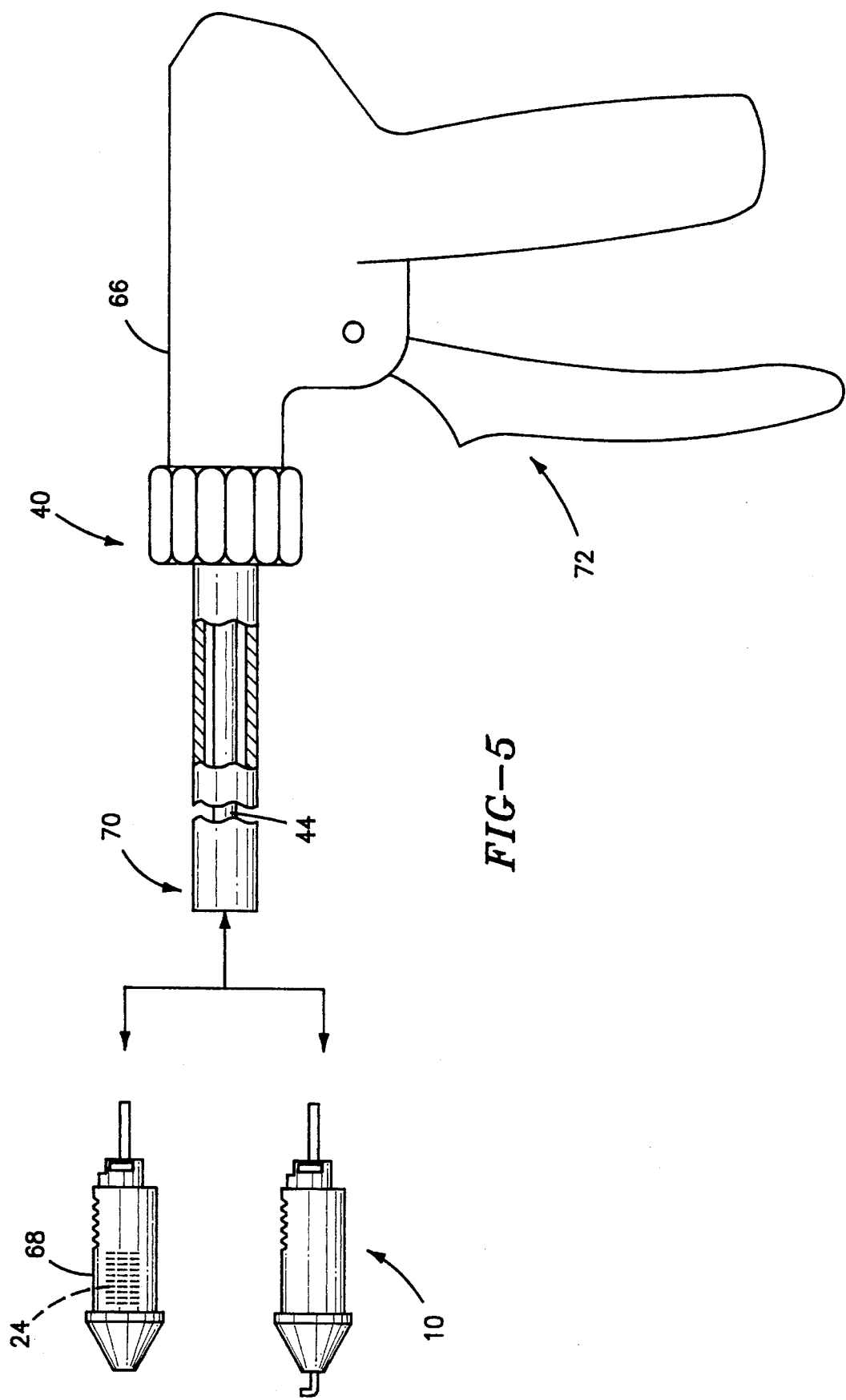
FIG. 5 is a schematic illustration of a surgical stapler and staple remover system in accordance with the invention.

FIG. 5 illustrates, partially schematically, a typical surgical stapler 40 having a body portion 66 and a stapler cartridge 68 carrying staples 24 for placement as desired. Stapler cartridge 68 is preferably releasably attachable to tubular end 70 of body member 66. Rod 44, as shown in the partially broken away portion of body member 66, is actuated, for example by trigger member 72, so as to operate stapler cartridge 68 thereby firing or discharging a staple to be placed in a desired location. In accordance with the invention, staple remover 10 is provided having similar structure for connection to end 70 of body member 66, and operation of staple remover 10 is actuated by similar motion to stapler cartridge 68, so that rod 44 may be used to operate staple remover 10 as well as stapler cartridge 68. In this way, if a staple is to be removed, body member 66 of stapler 40 may be used in conjunction with a staple remover 10 in a cartridge in accordance with the invention so as to remove staples from any location in which they may have been placed using stapler 40. Thus, advantageously, a system is provided in accordance with the invention whereby separate devices for removing staples are not required, and staples which have been placed in a location which is accessible to stapler 40 may likewise be removed using staple remover 10 connected to body member 66 of stapler 40.

In accordance with the foregoing, it should be noted that a staple remover 10 is provided in accordance with the invention which may be used advantageously to remove staples having non-straight or irregularly shaped bail portions 26 in a reliable and safe manner which avoids twisting and other undesirable displacement of a staple during removal. Of course, staple remover 10 is also advantageously useful with staples having straight bail portions. Further, a versatile system is presented in accordance with the invention wherein much of the same device used in installing staples is also useful in removing them.

It is apparent that there has been provided in accordance with this invention a staple remover which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A staple remover for removing surgical staples wherein said surgical staples have side members spaced from each other in a fired position at a staple spacing, said staple remover comprising: a housing;

a first arm having a first end and a second arm having a second end, said first and second arms being positioned within said housing so that said first and second ends extend from said housing at a first spacing which is less than said staple spacing; and means within said housing for laterally spreading said first and second ends so as to widen said first spacing of said first and second ends to a second spacing wider than said staple spacing wherein said means for laterally spreading is substantially coplanar with the first and second arms.

2. A staple remover according to claim 1, wherein said first end and said second end are biased toward said first spacing.

3. A staple remover according to claim 1, wherein said first arm and said second arm are resiliently joined within said housing so as to position said first end and said second end at said first spacing, and wherein said widening means is positionable between a starting position wherein said first end and said second end are at said first spacing and a widening position wherein said first end and said second end are deflected away from each other so as to widen said first spacing to said second spacing.

4. A staple remover according to claim 3, wherein said first end and said second end are biased toward said first spacing.

5. A staple remover according to claim 1, wherein said first and second arms have inwardly facing edges and wherein said widening means is positionable between a starting position wherein said first end and said second end are at said first spacing and a widening position wherein said widening means contacts said edges so as to space said first arm away from said second arm so as to provide said second spacing.

6. A staple remover according to claim 5, wherein said inwardly facing edges have inwardly tapered portions which taper toward each other and wherein said widening means comprises a pusher member slidably mounted in said housing between said first arm and said second arm and slidable between a forward position wherein said pusher member contacts said inwardly tapered portions so as to deflect said first end and said second end to said second spacing, and a rearward position wherein said pusher member is at least partially withdrawn from said inwardly tapered portions.

7. A staple remover according to claim 1, wherein said first end and said second end have prong members extending therefrom at an angle relative to said first arm and said second arm.

8. A staple remover according to claim 7, wherein said prong members have a terminal point and taper toward said terminal point whereby positioning said prong members within a staple is facilitated.

9. A staple remover according to claim 7, wherein said prong members extend at an angle of about 90°.

10. A staple remover according to claim 1, further comprising holding means for holding a staple in position relative to said first end and said second end whereby a staple may be held in position during removal.

11. A staple remover according to claim 10, wherein said holding means comprises a holding arm slidably positioned within said housing and spaced relative to said first and second arms, said holding arm being slidable between a withdrawn position and an extended position wherein said holding arm and said first and second arms define a gap therebetween for receiving and holding a staple.

12. A staple remover according to claim 11, wherein said widening means comprises a pusher member slidably positioned in said housing between said first arm and said second arm, and wherein said holding arm is slidably positioned above said pusher member.

13. A staple remover according to claim 12, further comprising means associated with said housing for limiting relative sliding of said pusher member relative to said holding arm.

14. A staple remover according to claim 13, wherein said limiting means comprises a slot on one of said pushing member and said holding arm, and a projection on the other of said pushing member and said holding arm, said projection extending into said slot so as to define a range of relative sliding of said pusher member relative to said holding arm.

15. A staple remover according to claim 1, wherein said housing comprises a cartridge adapted for releasable connection to a surgical stapler.

16. A staple remover according to claim 1, wherein said widening means comprises a pusher member slidably positioned in said housing for longitudinal sliding between a widening position wherein said pusher member deflects said first and second arms to said second spacing and a ready position wherein said first and second arms are at said first spacing.

17. A stapler and staple remover system, comprising:

a stapler cartridge housing a stapler assembly;

a body member for receiving and operating said stapler cartridge; and a staple remover cartridge for removing surgical staples having side members spaced from each other in a fired position at a staple spacing, said staple remover cartridge comprising a housing and a staple remover assembly in said housing, said staple remover assembly comprising a first arm having a first end and a second arm having a second end, said first and second arms being positioned within said housing so that said first and second ends extend from said housing at a first spacing which is less than said staple spacing; and means for widening said first spacing of said first and second ends to a second spacing wider than said staple spacing and including means for operatively and releasably connecting said staple remover cartridge to said body member, whereby said body member is useful in removing staples.

18. A staple remover cartridge for use with a surgical stapler having a releasable stapler attachment and a body member for receiving said stapler attachment, said staple remover cartridge comprising:

a housing;

staple removing means for removing surgical staples having side members spaced from each other in a fired position at a staple spacing, said staple removing means being positioned within said housing and comprising a first arm having a first end and a second arm having a second end, said first and second arms being positioned within said housing so that said first and second ends extend from said housing at a first spacing which is less than said staple spacing;

means for widening said first spacing of said first and second ends to a second spacing wider than said staple spacing; and means for releasably connecting said cartridge to the body member whereby said staple removing means may be operated with the body member.

19. A staple remover for removing surgical staples wherein said surgical staples have side members spaced from each other in a fired position at a staple spacing, said staple remover comprising:

a housing, wherein said housing comprises a cartridge adapted for releasable connection to a surgical stapler;

a first arm having a first end and a second arm having a second end, said first and second arms being positioned within said housing so that said first and second ends extend from said housing at a first spacing which is less than said staple spacing; and means for widening said first spacing of said first and second ends to a second spacing wider than said staple spacing.

20. A staple remover for removing surgical staples wherein said surgical staples have side members spaced from each other in a fired position at a staple spacing, said staple remover comprising:

a housing;

a first arm having a first end and a second arm having a second end, said first and second arms being positioned within said housing so that said first and second ends extend from said housing at a first spacing which is less than said staple spacing; and means for widening said first spacing of said first and second ends to a second spacing wider than said staple spacing, wherein said widening means comprises a pusher member slidably positioned in said housing for longitudinal sliding between a widening position wherein said pusher member deflects said first and second arms to said second spacing and a ready position wherein said first and second arms are at said first spacing.

21. A staple remover for removing surgical staples wherein said surgical staples have side members spaced from each other in a fired position at a staple spacing, said staple remover comprising:

a housing;

a first arm having a first end and a second arm having a second end, said first and second arms being positioned within said housing so that said first and second ends extend from said housing at a first spacing which is less than said staple spacing;

means for widening said first spacing of said first and second ends to a second spacing wider than said staple spacing; and holding means for holding a staple in position relative to said first end and said second end whereby a staple may be held in position during removal, wherein said holding means comprises a holding arm slidably positioned within said housing and spaced relative to said first and second arms, said holding arm being slidable between a withdrawn position and an extended position wherein said holding arm and said first and second arms define a gap therebetween for receiving and holding a staple.

* * * * *